(12) United States Patent
Dawood

(10) Patent No.: US 6,305,939 B1
(45) Date of Patent: Oct. 23, 2001

(54) IMPRESSION COPING SYSTEM FOR OSSEOINTEGRATED IMPLANTS

(75) Inventor: J. S. Andrew Dawood, London (GB)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/463,185

(22) PCT Filed: Jul. 8, 1998

(86) PCT No.: PCT/SE98/01344

§ 371 Date: Mar. 21, 2000

§ 102(e) Date: Mar. 21, 2000

(87) PCT Pub. No.: WO99/04723

PCT Pub. Date: Feb. 4, 1999

(30) Foreign Application Priority Data

Jul. 25, 1997 (GB) .................................................. 9715793
Sep. 12, 1997 (GB) .................................................. 9719508

(51) Int. Cl.[7] .................................. A61C 8/00; A61C 9/00
(52) U.S. Cl. ............................................ 433/174; 433/214
(58) Field of Search ..................................... 433/213, 214, 433/174, 172, 173

(56) References Cited

U.S. PATENT DOCUMENTS

| | | | |
|---|---|---|---|
| 4,850,870 | 7/1989 | Lazzara et al. . | |
| 4,955,811 | 9/1990 | Lazzara et al. . | |
| 5,009,596 | * 4/1991 | Soderberg | 433/174 |
| 5,125,841 | * 6/1992 | Carlsson et al. | 433/214 |
| 5,213,502 | * 5/1993 | Daftary | 433/214 |
| 5,334,024 | * 8/1994 | Niznick | 433/173 |
| 5,350,297 | 9/1994 | Cohen . | |
| 5,527,182 | 6/1996 | Willoughby . | |
| 5,658,147 | * 8/1997 | Phimmasone | 433/214 |
| 5,662,476 | 9/1997 | Ingber et al. . | |
| 5,674,073 | * 10/1997 | Ingber et al. | 433/213 |
| 5,685,715 | * 11/1997 | Beaty et al. | 433/173 |
| 5,688,123 | * 11/1997 | Meiers et al. | 433/214 |
| 5,755,574 | * 5/1998 | D'Alise | 433/174 |
| 5,759,036 | * 6/1998 | Hinds | 433/214 |
| 5,871,358 | 2/1999 | Ingber et al. . | |
| 5,904,483 | * 5/1999 | Wade | 433/214 |
| 5,938,443 | 8/1999 | Lazzara et al. . | |
| 6,068,478 | * 5/2000 | Grande et al. | 433/172 |

FOREIGN PATENT DOCUMENTS

| | | |
|---|---|---|
| 0 747 017 A2 | 12/1996 | (EP) . |
| 0 879 025 B1 | 9/1999 | (EP) . |
| WO 97/17907 | 5/1997 | (WO) . |

* cited by examiner

*Primary Examiner*—Todd E. Manahan
(74) *Attorney, Agent, or Firm*—Connolly Bove Lodge & Hutz

(57) ABSTRACT

The present invention relates to a system of interchangeable impression coping for use with osseointegrated implant systems. The coping system will allow an accurate registration of the fixture head, abutement, healing abutment, or other prefabricated components to which the implant may be connected. The coping system also permits the direct substitution of each of the various impression copings within an index or impression, so as to transfer, translate or transform the relations and/or the type of component to a model adapted from an index or poured from an impression registered using the coping system.

11 Claims, 4 Drawing Sheets

IMPRESSION COPING SYSTEM FOR OSSEOINTEGRATED IMPLANTS

Osseointegrated implants are fixtures commonly screwed into prepared sites in the jaw, facial, or limb bones for the retention of prostheses, e.g. dental bridges, facial prostheses, or limb prostheses. Such prostheses are usually retained by means of screws, adhesives, or mechanical attachments to an abutment, which is itself precisely located on and connected to the fixture by means of an abutment screw.

Figure 1:
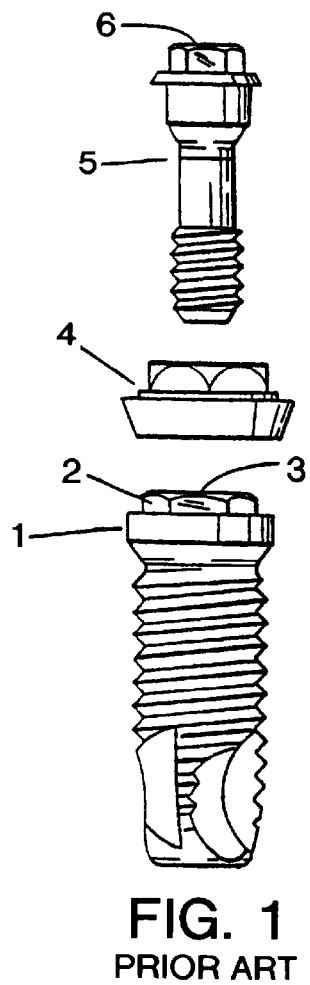
FIG. 1 shows a typical dental abutment of the prior art.
Figure 3:
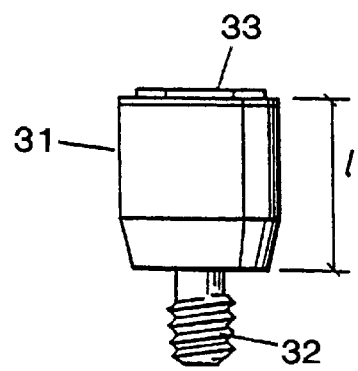
FIG. 3 shows a healing abutment of the prior art.
Figure 2A:
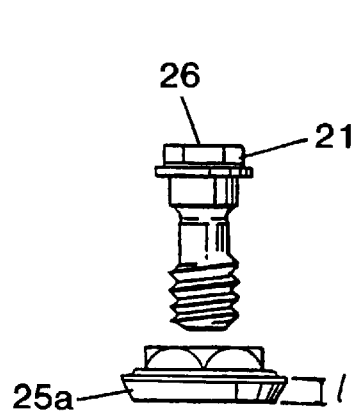
FIG. 2 shows prior art abutments of a type commonly used to support dental prothesis.
Figure 2B:
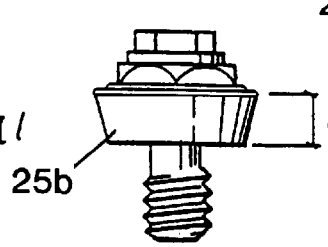
Figure 2C:
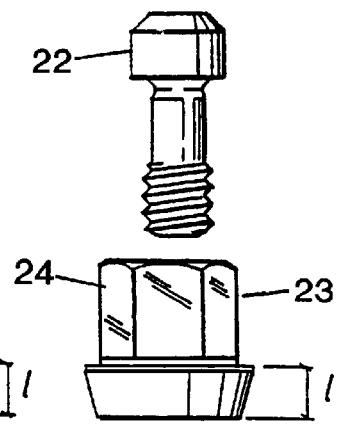
Figure 4:
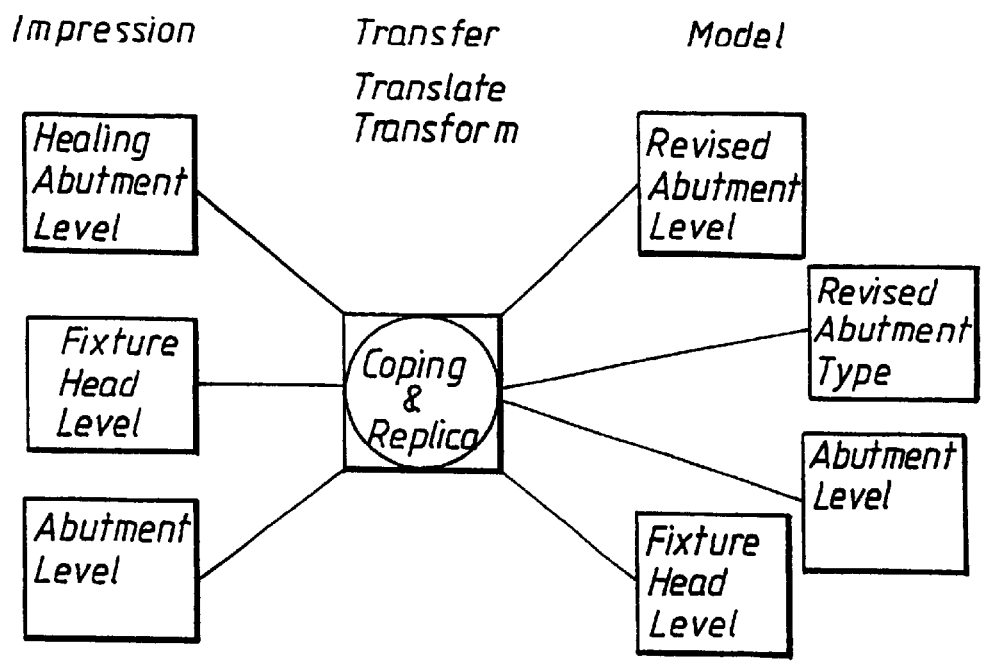
FIG. 4 is a chart depicting the process of using the system of the present invention.

An abutment is a trans-mucosal, or trans-dermal component, usually fabricated from a highly bio-compatible material capable of developing some kind of stable union with the adjacent living tissues, which facilitates the connection of the prosthesis to the fixture. Abutments may have a precise, prefabricated external configuration which will allow the use of prefabricated "prosthetic" components which precisely fit against the abutment for the fabrication of the prosthesis framework, or the abutment may be intended for preparation, in which case a framework may be constructed using conventional dental crown and bridge impression and fabrication techniques. Alternatively, a prosthesis may be fixed directly to the fixture head, using prefabricated "prosthetic" components which precisely fit against the fixture for the fabrication of the framework.

FIG. (1) illustrates a typical dental implant, and associated components by way of example. The head of the fixture (1) is provided with a hexagonal external feature (2), and a screw recess (3), which together allow the fixture to be manipulated, and permit the connection of an abutment (4), by means of an abutment screw (5). If the abutment is designed to allow screw retention of a prosthesis, the head of the abutment screw may itself contain a recess (6) for a prosthesis retention screw.

FIG. (2) illustrates abutments of a type commonly used to support dental prostheses. Both abutment types are connected to the fixture by means of an abutment screw (21 and 22). One abutment type (23) is designed for cementation of a restoration onto a suitably shaped part (24), and another type, (25a and 25b), is designed for screw retention of the restoration by means of a "prosthetic" screw which is screwed through the restoration into an appropriate recess in the abutment screw head (26). The abutment length in each case is 1. Apart from differences in general shape, abutments of each type are available in different lengths, as illustrated (25a and 25b).

The fixtures are usually placed as either a one stage surgical procedure, in which case the fixture, or an abutment connected to the fixture immediately protrudes through the skin or mucosa overlaying the site, or as a two stage procedure in which case the fixture is covered over with the overlaying tissue after installation (first stage surgery), and left to heal undisturbed for a period, at which time a second small surgical procedure, (second stage surgery) permits access to the head of the fixture, and an abutment, which protrudes through the tissue, is attached.

In areas of the mouth which are not cosmetically important, or in other situations where an abutment need not to be selected or prepared with precision, it is often possible to select or fit an abutment at the time of surgery, accepting that the final relationship of the abutments with the adjacent tissue may be less then ideal. There are other situations where an abutment may be placed, and subsequently replaced.

However it is often more convenient to allow the tissues (i.e. the gingivae for oral implants or skin for other fixtures) to heal before selecting the definitive abutment to which the prosthesis will be attached, as it is only after the tissues have healed, that an abutment of exactly the correct proportions may be predictably selected or prepared.

With this in mind, it is common practice to connect healing abutments, which are commonly formed of titanium, or a similary bio-compatible material, to the fixture, until the tissue has healed, and a relatively stable soft tissue contour has established. Healing abutments may be connected, either during one stage surgery, or at second stage surgery.

Healing abutments, which often have a solid one piece construction, usually screw into the head of the fixture and act as a solid template against which the tissues can heal. FIG. (3) illustrates a healing abutment, in which, a cylindrical body (31) tapers towards the fixture head, to which it is fixed by means of an integral abutment screw (32). A retentive feature (33) permits the healing abutment to be picked up and manipulated by a screw driver, and may permit the connection of various attachments. The length of the healing abutment (1) is selected to suit the height of the tissue collar around the fixture head. (Some healing abutments have a two piece construction, in which case the healing abutment per se is positioned over the head of the fixture, and may interlock with any anti-rotational features of the fixture head, and a retaining screw may then be screwed through the abutment and into the head of the fixture).

Once the tissues have healed an a stable tissue contour has established, and once a strong bony support for the fixture has developed, the paling abutment may be removed and the final abutment fitted.

Once the final abutment has been fitted, it is common practice for an impression to be taken so as to construct a detailed model of the protruding abutment and the surrounding tissue. This usually involves the connection of precise, prefabricated impression copings to the abutments, and taking an impression which picks up the impression copings in such a way that the abutments may be precisely related to the surrounding tissues, and to one another.

The impression is usually cast using an accurate material such as a dental model stone to create a model upon which the prostheses can be constructed. It is also common practice to use abutment replicas, which may be located within the matched impression coping so as to exactly replicate the important details of the abutment surface on the model.

An impression may also be registered, using impression copings which fit the fixture head, and a model formed using fixture replicas which emulate the relevant detail of the fixture head, facilitating the production of an accurate working model. A prosthesis may be constructed which is fitted directly onto the fixture heads, or abutments may be selected or prepared out of the patients mouth and the prosthesis constructed on the working model with the abutments in place.

This approach may be adapted so as to permit the position of the fixture heads to be registered upon completion of fixture installation. This means that abutments may be selected, and prepared if necessary, and then provisional or definitive restorations or prostheses fabricated, ready for insertion, either at the time of second stage surgery or following healing of the gingivae or skin around the healing abutment after fixture installation and following stabilisation of the fixture.

It is important to note that research has demonstrated a form of tissue attachment to the commercially pure titanium surface of the tissue penetrating abutments, and this has been shown to be somewhat fragile, as manipulating and swapping over components seems to cause loss of tissue attachment, and possibly increases remodeling of the adjacent tissues.

This invention comprises a system of interchangeable, fixture head impression copings, abutment impression copings, and healing abutment impression copings, which will allow an accurate registration of the fixture head, abutment, or healing abutment, and permits the direct substitution of each of the various impression copings within an index or impression, so as to apparently transfer, translate, or transform the relations of, and or the component type, to a model adapted from an index or poured from an impression registered using the coping system. This process is depicted in FIG. (4).

Figure 5A:
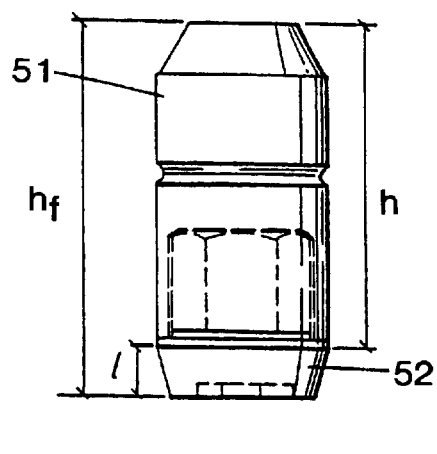
FIG. 5 shows an impression coping of the present invention.
Figure 5B:
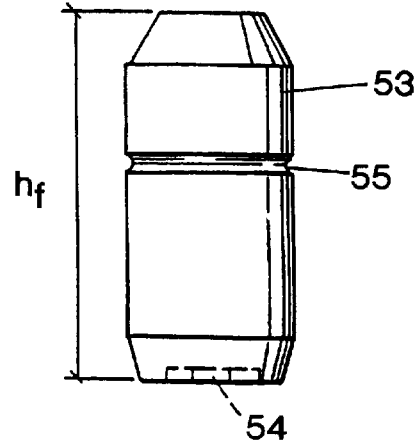
Figures 6A, 6B, 6C, 6D:
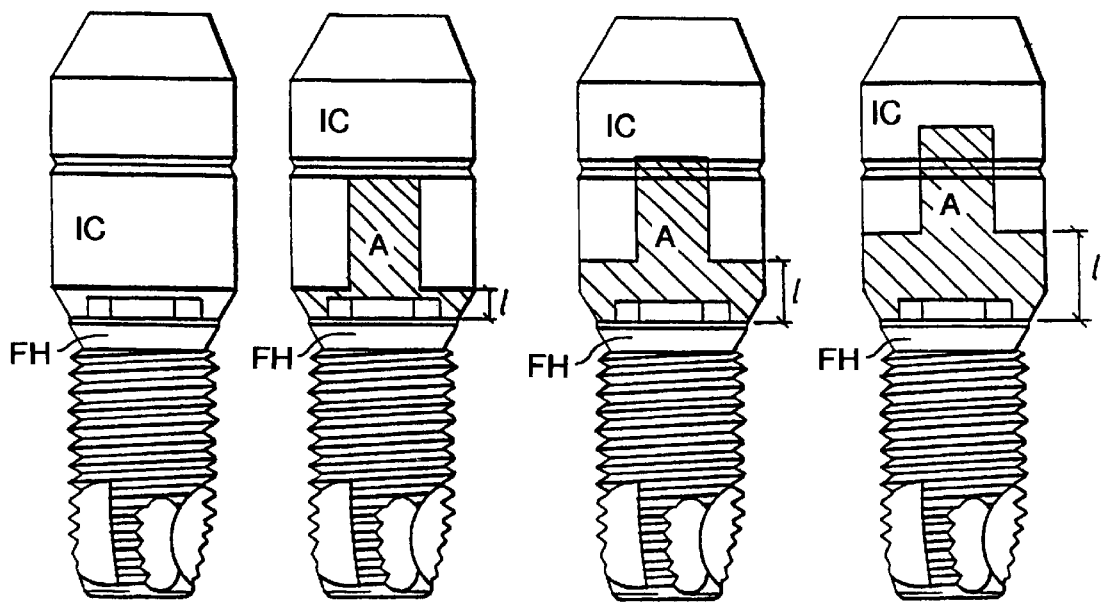
FIG. 6 shows impression copings fitted on abutments of different lengths.
Figures 7A, 7B, 7C:
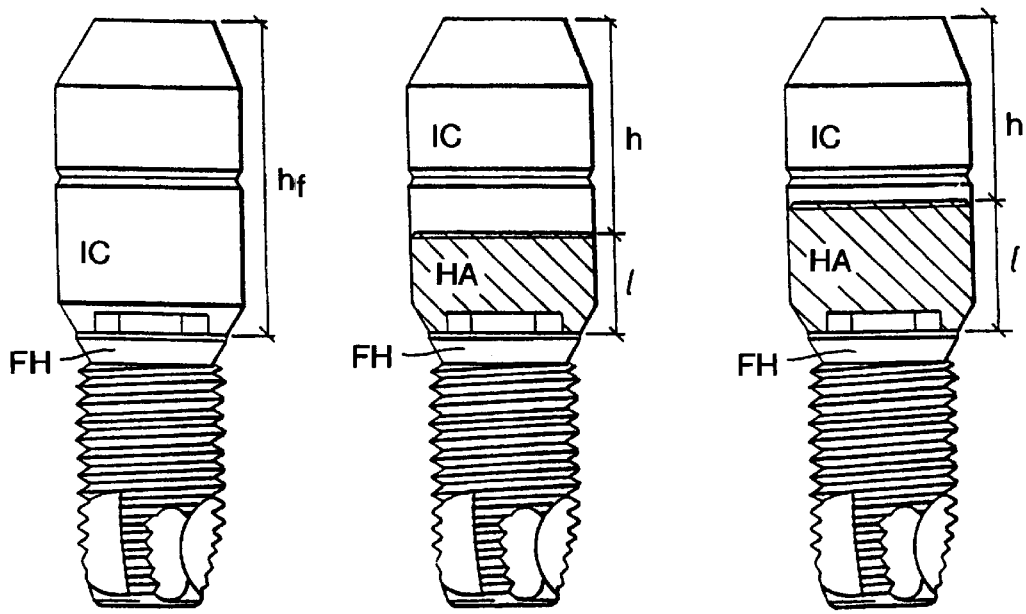
FIG. 7 shows impression copings fitted on the fixture head as well as on healing abutments of different lengths.

A specific embodiment of this invention will now be described with reference to FIGS. 5–7.

FIG. (5) illustrates an impression coping (51), height h, seated over an abutment, (52), length l, where the total height of the coping (h) plus the abutment length (l) is equal to a standardized value. This standard value is equivalent to a fundamental height $h_f$ which is the height of an impression coping (53), with a recess at its base (54) which is designed to locate directly over a fixture head.
Thus:

$$h+1=h_f$$

In all cases, a standardized retentive feature (55) situated at an identical location on each coping, permits the coping to be retained by an appropriate impression material capable of flowing into the feature. Above the retentive feature each coping is identical in size and shape. Below the retentive feature the coping is smooth sided and uniform in cross-section; the width of the copings at any point is also standardized, and is no less than that of the largest component upon which it may be located.

The component fitting surface of the copings may take many forms, which will permit the coping to precisely locate over a fixture head, abutment, healing abutment, or any other prefabricated component which may be located over the fixture head. The coping may be retained by friction or mechanical interlocking upon a retentive feature of the component, or by means of a retaining screw which passes through the coping, but maintains the standardized external dimensions and contour of the coping.

Apart from accommodating prefabricated components of different purpose and design, copings are provided of different heights, so as to accommodate components of different lengths, such that if the length of e.g. an abutment is increased, then the height of the coping is reduced accordingly. FIG. (6) demonstrates how copings (IC) located on abutments (A) of different length (l) are selected such that the total height of the coping and abutment together is identical to that of a coping located on a fixture head (FH).

This principal is also applied to healing abutments. FIG. (7) demonstrates an impression coping (IC), which is fitted to a fixture head (FH) as well as impression copings of various lengths which have been pushed into place on the retentive features of the occlusal aspect of healing abutments (HA) of different lengths. The external dimensions of the coping/healing abutment combinations is analogous to that of the fixture head impression coping.

With an impression coping of the correct height seated in place over a prefabricated component located on the fixture head, or on the fixture head itself, an impression may be taken of e.g. the jaw, which will "pick up" the impression coping as the impression material flows into the retentive feature. The coping may then be removed from the impression, and replaced with an alternative coping, to which an appropriate replica may be attached which will lock into place in an identical fashion, replicating the orientation that would exist with alternative components connected to the fixture head, or replicating the orientation of the fixture head itself.

In situations where the precise orientation of the external or internal anti-rotational features of a fixture must be established, the impression copings must also have an external shape which prevents rotation of the coping within the impression, and a component fitting surface that engages distinct features on the component. Use of the system is now described by way of example, using impression taking for the construction of a dental prosthesis as an example:

1. Fixture head impression copings may be attached to the fixture head immediately upon installation, or at any later date, and an impression or alternative form of index or registration taken.

Fixture head replicas may then be located within the coping, and a working model created, upon which abutments may be prepared or attached, and restorations may be constructed. This process transfers the relations of the fixture head from patient to model.

Alternatively, the impression coping may be removed, and an abutment level impression coping of particular type or length may be inserted in its place, and an appropriate abutment replica located within the coping. A working model may then be formed, which anticipates the connection of the planned abutments to the fixture heads, thus permitting preliminary stages of the construction of the restoration, or even a final restoration to be constructed, without having to handle the actual abutments in the laboratory. This process transforms and translates the relations of the fixture head in the jaw to a model which accurately demonstrates the relations that the selected abutment type would have if located onto the fixture head.

2. Healing abutment impression copings may be located on the occlusal aspect of Healing Abutments which have been connected to the fixture head either immediately upon installation of the fixture, or at the time of second stage surgery, (or subsequently). An impression or alternative form of index or registration may be taken once the soft tissues have been closed around the abutment at the time of surgery, or ideally after a period of healing and tissue maturation.

The healing abutment impression coping may then be removed from the impression, and an Abutment level or Fixture head level impression coping of particular type or length may be inserted in its place, an appropriate replica located within the coping. A working model may then be formed, which anticipates the connection of a planned abutment to the fixture head, or replicates the position of the fixture head itself. This process thus transforms and translates the relations of the healing abutment, fixture head, jaw, and adjacent soft tissue to a model which accurately demonstrates the relations of the fixture head, or the relations that the selected abutment type would have if located onto the fixture head.

If the tissues have been allowed to heal and mature following surgery, the final abutments may be predictably selected or prepared in the knowledge that there will be little further change in tissue contour, thus facilitating, and increasing the predictability of subsequent restorative stages.

3. Abutment impression copings may be located on the abutments and an impression or alternative form of index or registration taken which will pick up the impression copings.

Abutment replicas may then be located within the copings, and a working model formed, upon which restorations may be constructed. This process transfers the existing relations of the abutment from patient to model. Alternatively, if there is a need to change abutments, e.g. after shrinking of the soft tissues, the impression coping may be removed, and an abutment level impression coping of different type or length may be inserted in its place, and an appropriate abutment replica located within the coping. A working model may then be formed, which anticipates the replacement of the existing abutment with the planned abutment, thus minimising manipulation of components and the tissues. If necessary a fixture level coping may be placed, thus permitting preparation or selection of a new abutment on a laboratory model.

For an implant system comprising of many different fixture and abutment types and sizes many copings of the type described above will be required. A further embodiment of this invention is intended to overcome this potential drawback.

This alternative embodiment will now be described with reference to FIG. (8), in which a two part impression coping is seated over abutments of different lengths.

The main body of the coping (81) is seated over the abutment (83). Opposing vertical slots, (84 and 85) of different heights, are located in the walls of the coping body. The outer casing of the coping (82), fits over the body of the coping. On the inner aspect of the casing (82), spurs (86) are located such that the outer casing may be located over the body in two different orientations, as depicted in FIG. (8), A&B.

FIG. (8),A, shows the two part coping in place over a long abutment. In this case, the spurs (86) are located fully in the long slots (85), in the body of the coping.

Figure 8A:
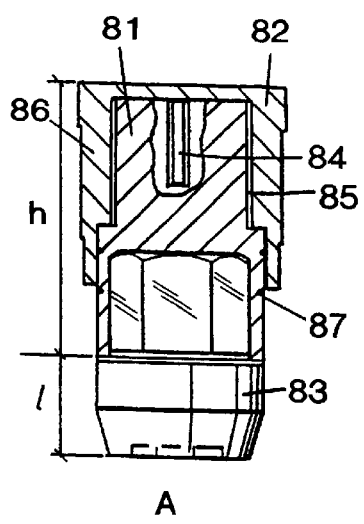
FIG. 8 shows an alternative embodiment of a two part impression coping seated over abutments of different lengths.
Figure 8B:
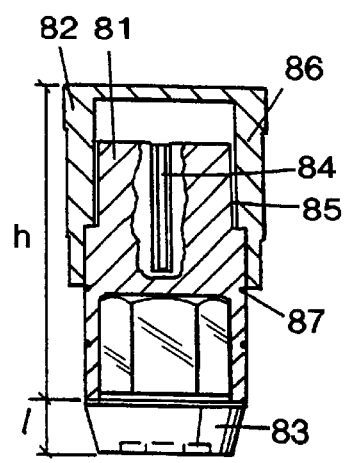
Figure 8C:
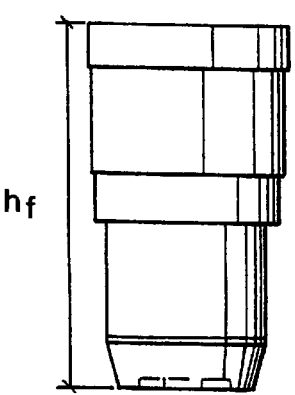

To convert the coping for use with a short abutment the two parts of the coping, (81 and 82) are pulled slightly apart so that the spurs (86) disengage the slots (85). The body (81) may then be rotated within the casing (82), such that the spurs (86) may be inserted into the short slots (84), thus lengthening the total height of the coping, as in FIG. 8,B. Different abutment heights may be catered for by varying the length and number of slots in the body of the coping.

To facilitate the use of the coping, markings (87) on the exterior the coping body, which are covered, or uncovered, depending on the state of extension of the casing, will tell the operator if the coping is correctly extended for use with the abutment in question.

There is also provided a fixture head coping, as depicted in FIG. (8),C. This is the fundamental coping for the system, as described elsewhere in this text. The external profile of this coping is essentially similar to that of the various different configurations of the two part coping and abutment or healing abutment combination; thus models may be constructed in a similar fashion to that described above.

What is claimed is:

1. A system of interchangeable impression copings for use with osseointegrated implant systems, comprising:
   at least a first impression coping having a component fitting surface mountable to at least a first type of component connectable to an osseointegrated implant; and
   at least a second impression coping having a component fitting surface mountable to at least a second type of said component different from said first type;
      wherein said first and second impression copings are substitutable for each other within an impression taken using either of said first or second impression copings.

2. The system of claim 1, wherein said components comprise at least one of a fixture head, abutment or healing abutment.

3. The system of claim 1, wherein said impression copings are mountable to said components by means of friction, mechanical interlocking, or screw retention.

4. The system of claim 1, wherein said first and second impression copings have at least one common exterior feature, said first and second impression copings being identical to each other for an extent adjacent to said common exterior feature, for enabling said first and second impression copings to be substitutable for each other in said impression.

5. The system of claim 4, said common exterior feature comprising a retention groove.

6. The system of claim 1, wherein said first and second impression copings comprise identical external retentive features enabling positions of anti-rotational features of said components to be transferred to an impression.

7. The system of claim 1, said first and second impression copings being mountable to a common standardized height on said components.

8. A configurable impression coping, comprising:
   a body with walls having opposing vertical slots of different lengths; and
   an outer casing fitting over said body and having inner spurs;
      wherein said impression coping is configurable to accommodate abutments of different sizes by orienting said spurs to engage selected ones of said slots.

9. The configurable impression coping of claim 8, wherein said impression coping is retainable on said abutment by at least one of friction, mechanical interlocking, and a screw.

10. The configurable impression coping of claim 8, said body comprising exterior markings for showing a state of extension of said outer casing.

11. A method for efficient fabrication of a prosthesis model, comprising:
   providing a range of impression copings, each having a component fitting surface mountable to a different type of component connectable to an osseointegrated implant;
   forming an impression using a selected coping of said range of impression copings;
   replacing said selected coping in said impression with an alternative coping of said range of impression copings; and
   forming said model utilizing said impression with said alternative coping.

* * * * *